United States Patent
Jo et al.

(10) Patent No.: US 9,549,942 B2
(45) Date of Patent: Jan. 24, 2017

(54) COMPOSITION FOR PREVENTING OR TREATING DEGENERATIVE BRAIN DISEASES INCLUDING COMPOUND DOWNREGULATING EXPRESSION OF BACE1 PROTEINS

(71) Applicant: RESEARCH & BUSINESS FOUNDATION SUNGKYUNKWAN UNIVERSITY, Suwon-si (KR)

(72) Inventors: Dong Gyu Jo, Gwangju-si (KR); Jong Sung Park, Bucheon-si (KR); Youngkwang Youn, Yongin-si (KR); Yuri Choi, Suwon-si (KR); Ui Jeong Yun, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/330,583

(22) Filed: Jul. 14, 2014

(65) Prior Publication Data

US 2015/0018297 A1    Jan. 15, 2015

(30) Foreign Application Priority Data

Jul. 15, 2013  (KR) .................. 10-2013-0083098
Jun. 9, 2014   (KR) .................. 10-2014-0069137

(51) Int. Cl.

| | |
|---|---|
| *A01N 43/04* | (2006.01) |
| *A61K 31/70* | (2006.01) |
| *A61K 31/7076* | (2006.01) |
| *A61K 31/155* | (2006.01) |
| *A61K 31/045* | (2006.01) |
| *A61K 31/165* | (2006.01) |
| *A61K 31/4184* | (2006.01) |
| *A61K 31/706* | (2006.01) |
| *A61K 31/7068* | (2006.01) |
| *A61K 31/708* | (2006.01) |
| *A61K 31/7064* | (2006.01) |

(52) U.S. Cl.
CPC ............ *A61K 31/7076* (2013.01); *A23L 33/10* (2016.08); *A61K 31/045* (2013.01); *A61K 31/155* (2013.01); *A61K 31/165* (2013.01); *A61K 31/4184* (2013.01); *A61K 31/706* (2013.01); *A61K 31/708* (2013.01); *A61K 31/7064* (2013.01); *A61K 31/7068* (2013.01)

(58) Field of Classification Search
None
See application file for complete search history.

(56) References Cited

U.S. PATENT DOCUMENTS

2012/0329834 A1* 12/2012 Blondel et al. ............... 514/345

FOREIGN PATENT DOCUMENTS

KR    10-2010-0040894 A    4/2010

OTHER PUBLICATIONS

Weiss et al. Cancer Research (1974), vol. 34, pp. 581-587.*
Reddy et al. Brain Research Reviews (2005), vol. 49, pp. 618-632.*
Yanker, Bruce A. "Mechanisms of neuronal degeneration in Alzheimer's disease." Neuron vol. 16 (1996): 921-932.
Hardy, John, et al. "Genetic dissection of Alzheimer's disease and related dementias: amyloid and its relationship to tau." Nature neuroscience vol. 1 No. 5 (1998): 355-358.
Selkoe, Dennis J. "Translating cell biology into therapeutic advances in Alzheimer's disease." Nature vol. 399 (1999): A23-A31.
Craven, Rebecca. "A solution to Alzheimer's disease?." Nature Reviews Neuroscience vol. 2 (2001): 533-533.
Small, David H., "Alzheimer's disease and Aβ toxicity: from top to bottom." Nature Reviews vol. 2 (2001): 595-598.
Oddo, Salvatore, et al. "Triple-transgenic model of Alzheimer's disease with plaques and tangles: intracellular Aβ and synaptic dysfunction." Neuron vol. 39 (2003): 409-421.
Youn, Young Kwang, "Screening and characterization of β-secretase expression regulating chemicals", The Graduate School, Department of Pharmacy, Sungkyunkwan University, Apr. 2012 (11 pages).

* cited by examiner

*Primary Examiner* — Patrick Lewis

(57) ABSTRACT

The present disclosure relates to a pharmaceutical composition, a health functional food composition, and a method for preventing or treating a brain disease or diabetes. The pharmaceutical composition, health functional food composition, and method includes at least one active ingredient that is chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, or topotecan.

5 Claims, 13 Drawing Sheets

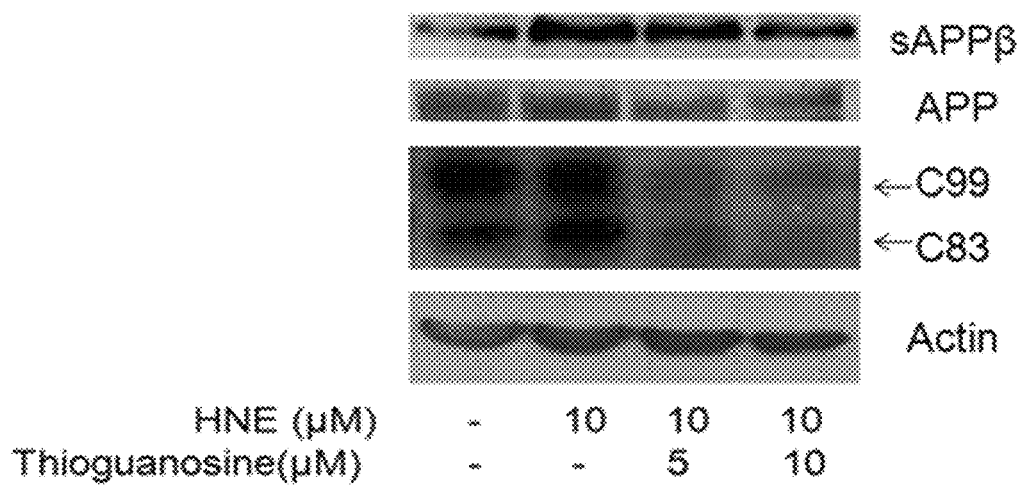
FIG. 12
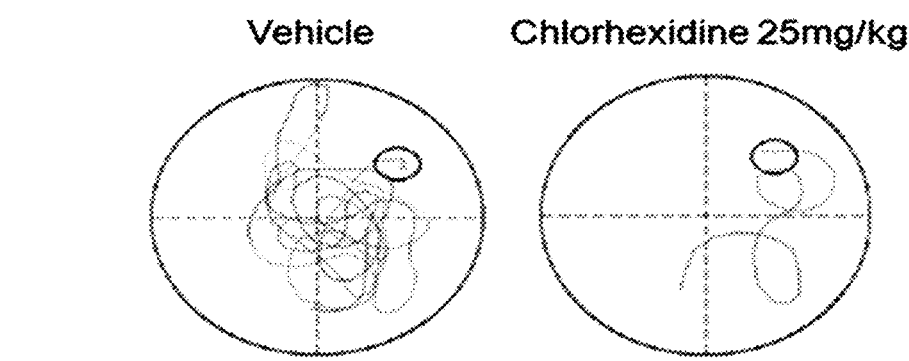
FIG. 13
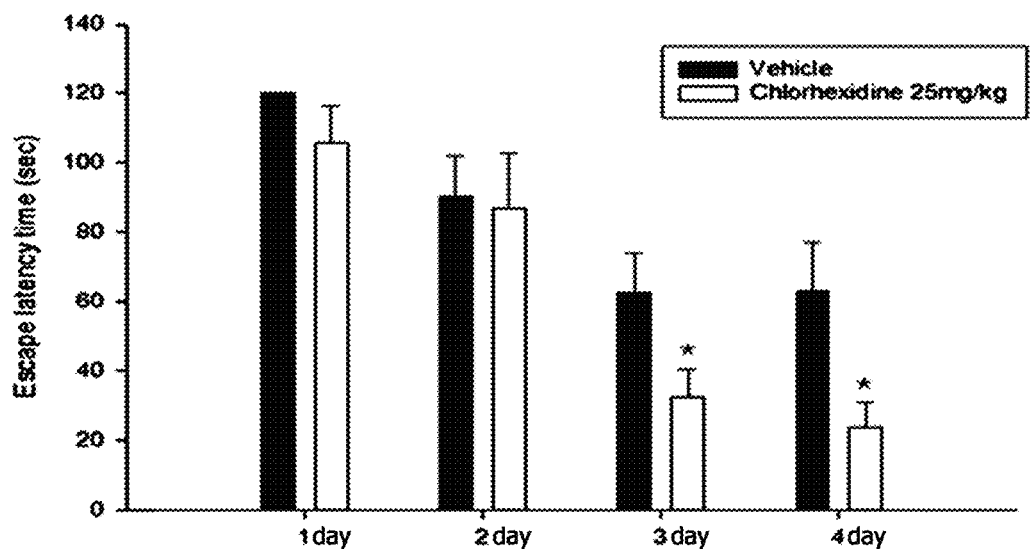

Vehicle

Chlorhexidine 25mg/kg

COMPOSITION FOR PREVENTING OR TREATING DEGENERATIVE BRAIN DISEASES INCLUDING COMPOUND DOWNREGULATING EXPRESSION OF BACE1 PROTEINS

CROSS-REFERENCE TO RELATED APPLICATION

This application claims priority to and the benefit under 35 USC 119(a) of Korean Patent Application No. 10-2013-0083098, filed on Jul. 15, 2013 and 10-2014-0069137 filed on Jun. 9, 2014, in the Korean Intellectual Property Office, the entire disclosures of which are incorporated herein by reference for all purposes.

BACKGROUND

1. Field

The following description relates to a composition for preventing or treating brain diseases or diabetes, and more specifically, a pharmaceutical composition or a food composition for preventing or treating degenerative brain diseases or diabetes containing a compound for downregulating expression of BACE1 proteins. The following description also relates to a method for preventing or treating a degenerative brain disease or diabetes, comprising administering a pharmaceutical composition to a subject in need thereof, wherein the pharmaceutical composition decreases expression of BACE1 proteins.

2. Description of Related Art

In the United States, Alzheimer's dementia (Alzheimer's disease) has a prevalence of about 3% in people aged 65 to 74, about 19% in people aged 75 to 84, and about 50% in people aged 85 or over. In Korea, according to a recent report focusing on rural areas, symptoms of dementia has a prevalence of about 21% in people aged 60 or over, and 63% of those have Alzheimer's dementia.

Such Alzheimer's dementia is a disease accounting for 50 to 70% of dementia, which causes gradual degeneration of nerve cells and loss of cognitive ability. Alzheimer's dementia may be classified as familial Alzheimer's dementia, due to genetic factors, or sporadic Alzheimer's dementia, of which causes are not accurately known and which occurs in a great number of patients. Alzheimer's dementia patients may show a memory loss and psychological symptoms such as mental abnormality including increased anxiety and a hypersensitivity reaction, which results in a complex cognitive defect. In the brains of patients who have died of Alzheimer's dementia, pathological evidence of senile plaque and neurofibrillary tangles may be visible. According to present understanding, senile plaque is formed by extracellular accumulation of proteins, dead cells, and the like. A main component thereof is amyloid beta peptides (Aβ) (Hardy, J. et al, Nat. Neurosci. 1:355-358, 1998).

A gradual loss of a cognitive reaction, which is a main feature of Alzheimer's dementia patients, is caused by abnormally accumulated Aβ. Aβ deposited in the brains of Alzheimer's dementia patients is generated from amyloid precursor proteins (APPs) through a proteolysis process. An APP is decomposed by beta-secretase (BACE1) and gamma-secretase (γ-secretase), and Aβ is generated (Craven, R., Nat. Rev. Neurosci. 2: 533, 2001; Small, D. H. et al., Nat. Rev. Neurosci. 2: 595-598, 2001; Yankner, B. A., Neuron 16: 921-932, 1996; Selkoe, D. J., Nature 399: A23-A31, 1999).

Accordingly, a substance for decreasing expression of beta-site APP-cleaving enzyme 1 (BACE1) that generates Aβ causing Alzheimer's dementia disease may be used as an agent for preventing and treating Alzheimer's dementia.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In view of the above-described related art, the present disclosure provides a pharmaceutical composition, and a health functional food composition, for preventing or treating degenerative brain diseases or diabetes including chlorhexidine, thioguanosine, mebendazole, fenbendazole, colchicine, and the like, which decrease expression of beta-secretase (BACE1) generating amyloid beta peptides (Aβ), as active ingredients. The present disclosure also provides a method for preventing or treating a degenerative brain disease or diabetes, comprising administering a pharmaceutical composition to a subject in need thereof, wherein the pharmaceutical composition decreases expression of BACE1 proteins In a general aspect, a pharmaceutical composition for preventing or treating a degenerative brain disease or diabetes includes at least one active ingredient selected from the group consisting of chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan.

The pharmaceutical composition may decrease expression of BACE1 proteins.

The pharmaceutical composition may suppress generation of amyloid beta peptides (Aβ).

The brain disease may be Alzheimer's dementia (Alzheimer's disease).

The pharmaceutical composition may further include a pharmaceutically acceptable carrier.

In another general aspect, a health functional food composition, for preventing or improving a degenerative brain disease or diabetes, includes at least one active ingredient selected from the group consisting of chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan.

The health functional food composition may decrease expression of BACE1 proteins.

The health functional food composition may suppress generation of amyloid beta peptides (Aβ).

In another general aspect, a method for preventing or treating a degenerative brain disease or diabetes includes administering a pharmaceutical composition to a subject in need thereof, wherein the pharmaceutical composition decreases expression of BACE1 proteins.

The method may include administering the pharmaceutical composition with an active ingredient including chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, or topotecan.

The method may include administering the active ingredient including a guanidine compound that is chlorhexidine, thioguanosine, mebendazole, or fenbendazole.

The method may include administering the active ingredient that is chlorhexidine or thioguanosine.

The method may suppress generation of amyloid beta peptides (Aβ).

The method may be directed to Alzheimer's dementia (Alzheimer's disease).

Other features and aspects will be apparent from the following detailed description, the drawings, and the claims.

BRIEF DESCRIPTION OF THE DRAWINGS

The above and other objects and features will become more apparent to those of ordinary skill in the art by describing in detail examples with reference to the accompanying drawings.

FIG. 12 is a western blot result that shows the result obtained by determining generation of APP CTFs by thioguanosine treatment under oxidative stress conditions of brain nerve cells in Example 3.

FIG. 13 is a diagram and graph that show the result obtained by determining a change in a learning ability by chlorhexidine treatment in an Alzheimer's dementia animal model in Example 4.

Throughout the drawings and the detailed description, unless otherwise described or provided, the same drawing reference numerals or abbreviations will be understood to refer to the same elements, features, and structure.

DETAILED DESCRIPTION

Figure 1:
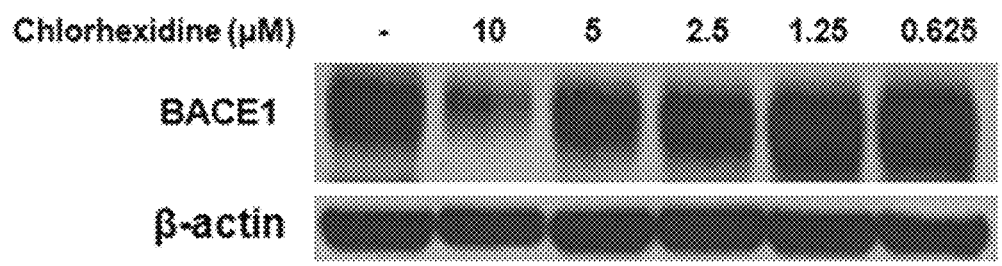
FIG. 1 is a western blot result that shows the result obtained by determining a change in an amount of expression of BACE1 proteins by chlorhexidine treatment in brain nerve cells in Example 1.
Figure 2:
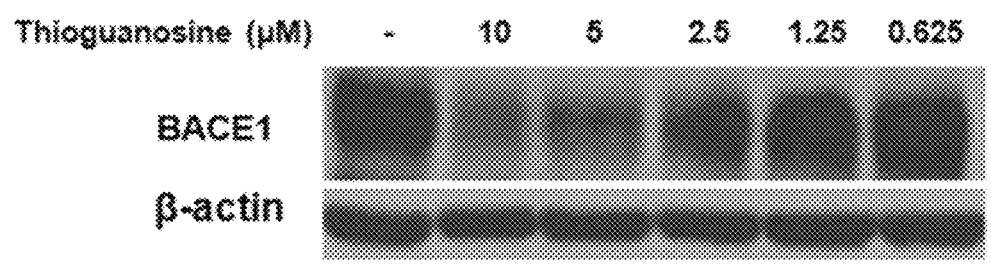
FIG. 2 is a western blot result that shows the result obtained by determining a change in an amount of expression of BACE1 proteins by thioguanosine treatment in brain nerve cells in Example 1.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The inventors have studied substances that decrease expression of BACE1 generating Aβ causing Alzheimer's dementia diseases. And the inventors have confirmed that substances such as chlorhexidine, thioguanosine, mebendazole, fenbendazole, colchicine, and the like, which were used for other purposes, decrease expression of BACE1 proteins. The present disclosure is completed based on the findings.

The present disclosure is related to a pharmaceutical composition for preventing or treating degenerative brain diseases or diabetes including at least one active ingredient selected from the group consisting of chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan. The brain diseases related to the present disclosure may include stroke, and preferably may include Alzheimer's dementia, but the brain diseases are not limited thereto.

The term "prevention" used in this specification refers to any action that suppresses and delays the onset of degenerative brain diseases or diabetes by administering the composition of the present disclosure.

The term "treatment" used in this specification refers to any action that improves or beneficially changes symptoms of degenerative brain diseases or diabetes by administering the composition of the present disclosure.

The active ingredient of the pharmaceutical composition according to the present disclosure may decrease expression of BACE1 proteins in an Alzheimer's dementia animal model and brain nerve cells, and may suppress generation of amyloid beta peptides (Aβ). Further, since it is well known that expression of BACE1 proteins affects development of diabetes, the composition according to the present disclosure may be usefully used as a composition for preventing, improving, or treating diabetes.

The pharmaceutical composition according to the present disclosure may include chlorhexidine as an active ingredient. Chlorhexidine N',N''''-hexane-1,6-diylbis[N-(4-chlorophenyl)(imidodicarbonimidic diamide)] is represented by the following Chemical Formula 1, a molecular weight (MW) is 505.46, and a CAS number is 55-56-1.

[Chemical Formula 1]

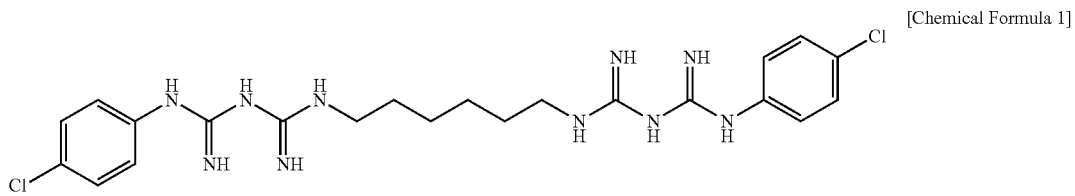 [SMILES: N=C(NCCCCCCNC(=N)NC(=N)Nc1ccc(Cl)cc1)NC(=N)Nc1ccc(Cl)cc1]

The pharmaceutical composition according to the present disclosure may include thioguanosine as an active ingredient. Thioguanosine is represented by the following Chemical Formula 2, a molecular formula is $C_{10}H_{13}N_5O_4S$, a molecular weight (MW) is 299.31, and a CAS number is 85-31-4.

[Chemical Formula 2]

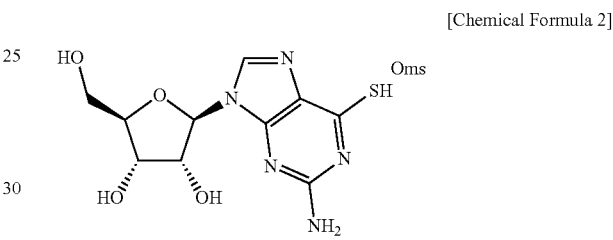

The pharmaceutical composition according to the present disclosure may include mebendazole as an active ingredient. Mebendazole is represented by the following Chemical Formula 3, a molecular formula is $C_{16}H_{13}N_3O_3$, a molecular weight (MW) is 295.30, and a CAS number is 31431-39-7.

[Chemical Formula 3]

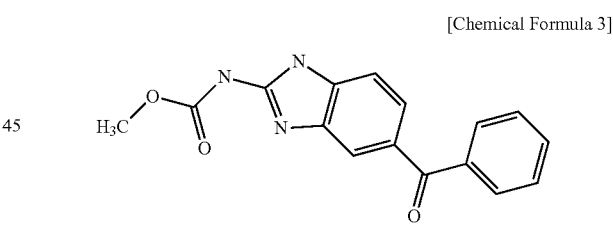

The pharmaceutical composition according to the present disclosure may include fenbendazole as an active ingredient. Fenbendazole is represented by the following Chemical Formula 4, a molecular formula is $C_{15}H_{13}N_3O_2S$, a molecular weight (MW) is 299.35, and a CAS number is 43210-67-9.

[Chemical Formula 4]

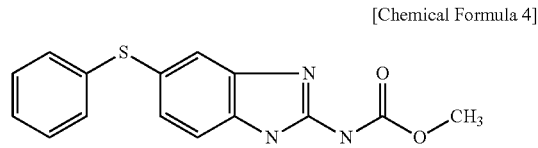 [SMILES: COC(=O)Nc1nc2cc(Sc3ccccc3)ccc2[nH]1]

An active ingredient of the pharmaceutical composition may be a guanidine compound selected from the group consisting of chlorhexidine, thioguanosine, mebendazole, and fenbendazole. Other guanidine compounds having a property of decreasing expression of BACE1 proteins or of suppressing generation of amyloid beta peptides (Aβ) to may be used as an active ingredient.

The pharmaceutical composition according to the present disclosure may include colchicine as an active ingredient. Colchicine is represented by the following Chemical Formula 5, a molecular formula is $C_{22}H_{25}NO_6$, a molecular weight (MW) is 399.45, and a CAS number is 64-86-8.

[Chemical Formula 5]

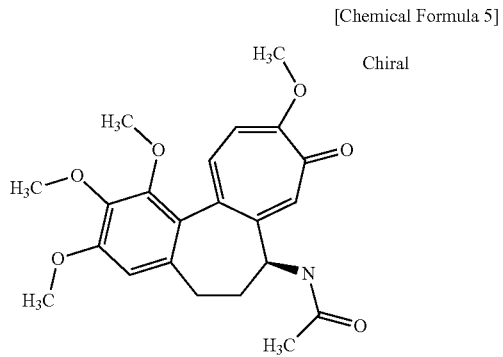 [SMILES: COc1cc2c(c(OC)c1OC)-c1ccc(OC)c(=O)cc1[C@@H](NC(C)=O)CC2]

The pharmaceutical composition according to the present disclosure may include farnesol as an active ingredient. Farnesol is represented by the following Chemical Formula 6, a molecular formula is $C_{15}H_{26}O$, a molecular weight (MW) is 222.37, and a CAS number is 4602-84-0.

[Chemical Formula 6]

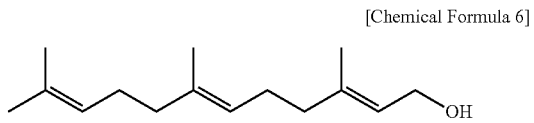 [SMILES: CC(C)=CCC/C(C)=C/CC/C(C)=C/CO]

The pharmaceutical composition according to the present disclosure may also include trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, topotecan, and the like, as active ingredients.

Meanwhile, the described compounds may be prepared by the known chemical synthetic methods or a commercially available reagent (Kingston Chemistry, USA) may be used.

The pharmaceutical composition according to the present disclosure may include one or more of the above active ingredients.

Referring to the Examples of the present disclosure, chlorhexidine, thioguanosine, mebendazole, fenbendazole, colchicine, and farnesol decrease an amount of expression of BACE1 proteins in brain nerve cells (refer to Example 1), and chlorhexidine and thioguanosine decrease an amount of BACE1 expression under oxidative stress conditions of brain nerve cells (refer to Example 2). In addition, chlorhexidine and thioguanosine improve a learning ability and memory in the Alzheimer's dementia animal model (refer to Example 4). And chlorhexidine decreases an amount of BACE1 expression in the Alzheimer's dementia animal model (refer to Example 5), and suppresses generation of Aβ (refer to Example 6). Moreover, chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan decrease a BACE1 promoter activity by 50% or more in brain nerve cells (refer to Example 7).

The pharmaceutical composition according to the present disclosure may include a pharmaceutically acceptable carrier in addition to the active ingredient. As the pharmaceutically acceptable carrier included in the pharmaceutical composition according to the present disclosure, a saline, a buffered saline, water, glycerol, polyethylene glycol, a vegetable oil, isopropyl myristate, ethanol, and the like may be used, but the carrier is not limited thereto.

The pharmaceutical composition according to the present disclosure may be formulated using diluting agents or excipients such as commonly used fillers, extending agents, bonding agents, wetting agents, disintegrating agents, surfactants, and the like.

Solid formulations for oral administration may include tablets, pills, powders, granules, capsules, troches, and the like. Such solid formulations may be formulated by mixing at least one excipient, for example, a starch, calcium carbonate, sucrose, lactose, or gelatin, with peptides according to the present disclosure. Also, in addition to simple excipients, lubricants such as magnesium stearate and talc may be used. Liquid formulations for oral administration may include suspensions, liquids for internal use, emulsions, syrups, and the like. In addition to commonly used simple diluting agents such as water and liquid paraffin, several excipients, for example, wetting agents, sweetening agents, aromatics, and preserving agents, may be included.

Formulations for parenteral administration may include sterilized aqueous solutions, nonaqueous solvents, suspending agents, emulsions, freeze-dried formulations, suppositories, and the like.

As the nonaqueous solvents and the suspending agents, propylene glycol, polyethylene glycol, and vegetable oils such as olive oil, and injectable esters such as ethyl oleate may be used. As suppository bases, witepsol, macrogol, tween 61, cocoa butter, laurin, glycerol, gelatin, and the like may be used.

The composition according to the present disclosure may be administered orally or parenterally (for example, intraveneously, subcutaneously, intraperitoneally, or locally administered). A dose may vary depending on a subject's condition, body weight, degree of disease, drug form, administration route, and time. A suitable dose may be appropriately selected by those skilled in the art.

The composition according to the present disclosure may be administered in a pharmaceutically effective amount. The term "pharmaceutically effective amount" in this specification refers to an amount sufficient for treating diseases in a reasonable benefit/risk ratio applicable to medical treatment. A level of an effective dose may be determined by the patient's types of disease, severity of disease, a drug activity, drug sensitivity, an administration time, an administration route, an excretion ratio, a treatment period, factors including (an)other simultaneously used drug(s), and other factors well-known in the field of medicine. The composition according to the present disclosure may be administered as an individual treating agent, in combination with other therapeutic agents, sequentially or simultaneously administered with a conventional therapeutic agent, and administered at single or multiple times. It is important to administer an amount that can obtain a maximum effect with a minimum amount without side effects in consideration of all of the above factors. This may be determined by those skilled in the art.

Specifically, an effective dose of the composition according to the present disclosure may vary depending on the patient's age, sex, and body weight, and, generally, may be administered at 0.001 to 150 mg per kg of body weight, and preferably 0.01 to 100 mg daily or every other day, or may be divided into one to three times per day. However, since an administration dose may increase or decrease depending on the administration route, severity of disease, and the subject's sex, body weight, age, and the like, the scope of the present disclosure is not necessarily limited to an administration dose.

As another aspect, the present disclosure provides a health functional food composition for preventing or improving degenerative brain diseases or diabetes including at least one active ingredient selected from the group consisting of chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt (10b2), monensin sodium salt, raloxifene hydrochloride, 2-chloropyrazine, and topotecan. In order to prevent or improve degenerative brain diseases, the health functional food composition according to the present disclosure may be used before or after the onset of degenerative brain diseases, along with or separately from medicine for treating degenerative brain diseases.

The term "improvement" used in this specification refers to any action that decreases parameters related to a treatment state, for example, to at least decrease a severity of symptoms.

Since the health functional food composition according to the present disclosure decreases expression of BACE1 proteins and suppresses generation of Aβ, it may be added to dietary supplements such as food and drink in order to prevent or improve degenerative brain diseases.

Types of the food are not particularly limited. Examples of food to which the active ingredient may be added include drinks, meats, sausages, breads, biscuits, rice cakes, chocolates, candies, snacks, cookies, pizzas, noodles, other noodles, gums, milk-based products including ice creams, various soups, beverages, alcoholic drinks, vitamin complexes, dairy products, and dairy manufactured products, and include all health functional foods in a general meaning.

In the health functional food composition according to the present disclosure, the active ingredient may be directly added to food, used along with another food or food components, and appropriately used by general methods. A mixing amount of the active ingredient may be appropriately determined by usage purposes thereof (for prevention or improvement). In general, when a food or drink is produced, a proportion of the composition of the present disclosure may be 15 wt % or less, and preferably 10 wt % or less, with respect to a raw substance of the food or drink. However, in long-term intake for health and hygiene or health control, the amount may be equal to or less than the above range.

Components of a nutritional drink composition of the present disclosure are not limited other than that the active ingredient be contained as an essential ingredient in an indicated ratio. Similar to conventional drinks, additional ingredients may include several flavouring agents, a natural carbohydrate, and the like may. Examples of the natural carbohydrate include monosaccharides (for example, glucose and fructose), disaccharides (for example, maltose and sucrose), polysaccharides, conventional sugars (for example, dextrin and cyclodextrin), and sugar alcohols (for example, xylitol, sorbitol, and erythritol). In addition to the above ingredients, natural flavouring agents (thaumatin, stevia extract (for example, rebaudioside A and glycyrrhizin)) and synthetic flavouring agents (such as saccharin and aspartame) may be usefully used as the flavouring agent. A ratio of the natural carbohydrate may be appropriately selected and determined by those skilled in the art.

In addition to the above ingredients, the health functional food composition of the present disclosure may contain several nutritional supplements, vitamins, minerals (electrolytes), flavors such as synthetic flavors or natural flavors, coloring agents, and mogul agents (such as cheeses and chocolates), pectic acid and salts thereof, alginic acid and salts thereof, an organic acid, protective colloidal thickeners, pH adjusting agents, stabilizers, preservatives, glycerin, alcohol, carbonated agents used for carbonated drinks, and the like. These components may be used alone or in various combinations. A ratio of such additives may also be appropriately selected by those skilled in the art.

Hereinafter, particular examples of the present disclosure will be described for promoting an understanding of the present disclosure. However, the following examples are provided promote understanding of the present disclosure, and the scope of the invention is not limited to the following examples.

EXAMPLE

Example 1

Verification of an Influence of Chlorhexidine, Thioguanosine, Mebendazole, Fenbendazole, Colchicine, and Farnesol on an Amount of Expression of BACE1 Proteins in Brain Nerve Cells In order to determine an influence of chlorhexidine, thioguanosine, mebendazole, fenbendazole, colchicine, and farnesol of the present disclosure on BACE1 proteins in brain nerve cells, the following experiment was performed.

As brain nerve cells, human neuroblastoma cells SH-SY5Y were used. The SH-SY5Y cells were added to a culture solution including a DMEM media (4 mM L-glutamine, 4500 mg/L glucose, and sodium pyruvate), 10% FBS, and 1% penicillin streptomycin, and maintained in an incubator at 37° C. and 5% $CO_2$. The SH-SY5Y cells were plated at $5 \times 10^5$ cells/well into a 6-well plate. Chlorhexidine, thioguanosine, mebendazole, fenbendazole, and colchicine were used as treatments in concentrations of 0.625 μM, 1.25 μM, 2.5 μM, 5 μM, and 10 μM, and farnesol was used as a treatment in concentrations of 0.001 μM, 0.01 μM, and 0.1 μM for 24 hours. Then, the amount of expression of BACE1 proteins was determined by Western blot. Actin was used throughout as a control. FIGS. 1 to 6 show the results.

Figure 3:
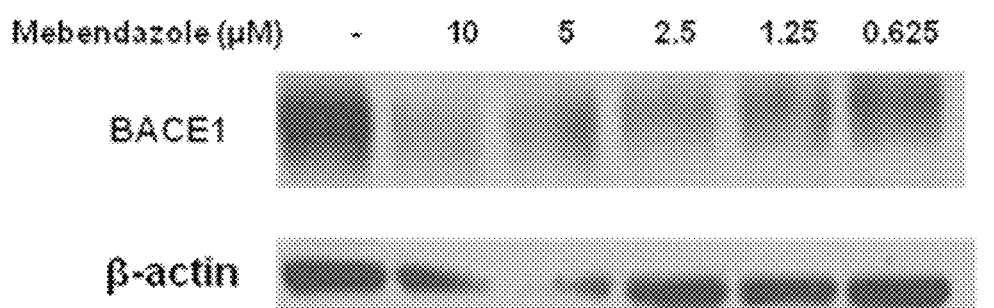
FIG. 3 is a western blot result that shows the result obtained by determining a change in an amount of expression of BACE1 proteins by mebendazole treatment in brain nerve cells in Example 1.
Figure 4:
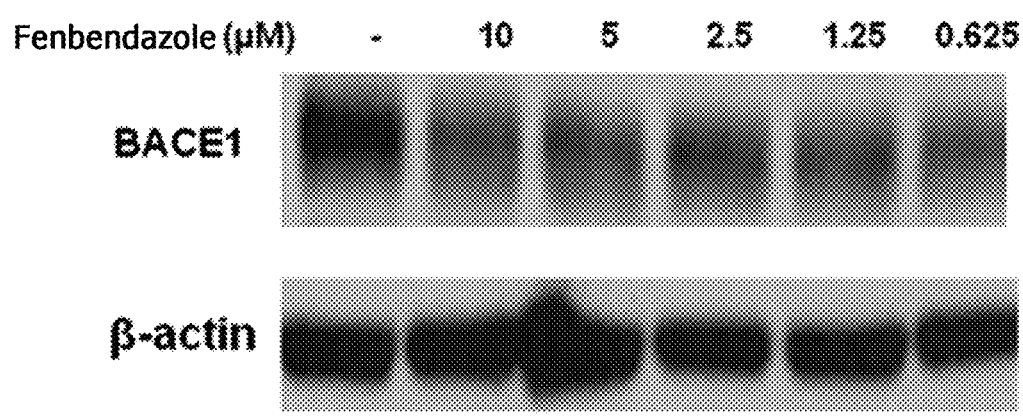
FIG. 4 is a western blot result that shows the result obtained by determining a change in an amount of expression of BACE1 proteins by fenbendazol treatment in brain nerve cells in Example 1.
Figure 5:
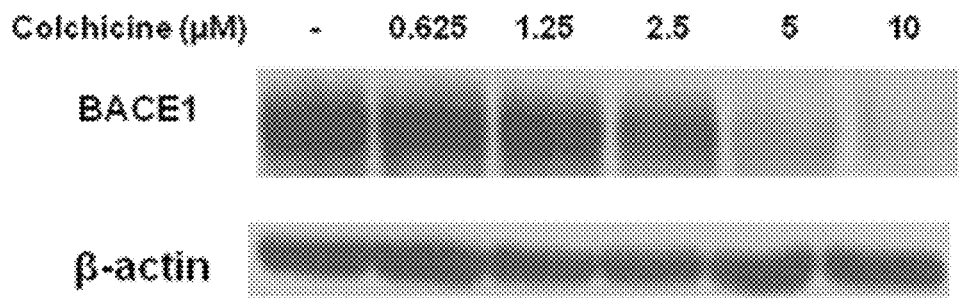
FIG. 5 is a western blot result that shows the result obtained by determining a change in an amount of expression of BACE1 proteins by colchicine treatment in brain nerve cells in Example 1.
Figure 6:
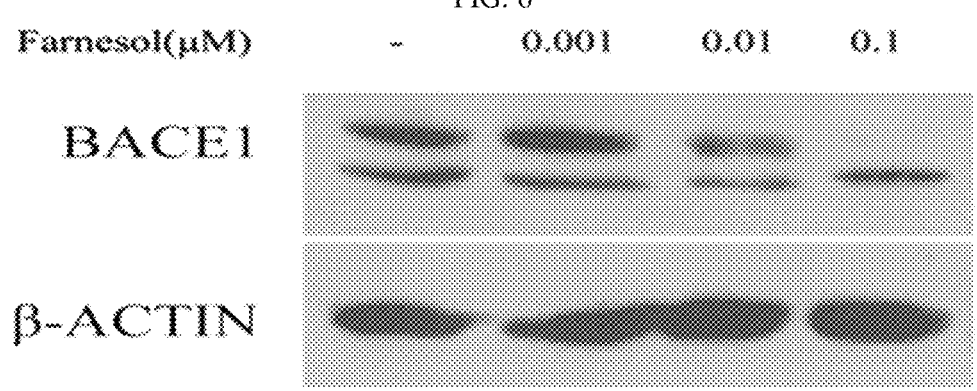
FIG. 6 is a western blot result that shows the result obtained by determining a change in an amount of expression of BACE1 proteins by farnesol treatment in brain nerve cells in Example 1.

As shown in FIGS. 1 to 6, when chlorhexidine was used as the treatment, the amount of expression of BACE1 proteins decreased at 5 μM and 10 μM (refer to FIG. 1). When thioguanosine was used as the treatment, the amount of expression of BACE1 proteins decreased at 2.5 μM, 5 μM, and 10 μM (refer to FIG. 2). Also, when mebendazole or fenbendazole was used as the treatment, the amount of expression of BACE1 proteins decreased at 0.625 μM to 10

μM (refer to FIGS. 3 and 4). In addition, when colchicine was used as the treatment, the amount of expression of BACE1 proteins decreased at 5 μM and 10 μM (refer to FIG. 5). When farnesol was used as the treatment, the amount of expression of BACE1 proteins decreased at 0.01 μM and 0.1 μM (refer to FIG. 6).

Example 2

Verification of an Influence of Chlorhexidine and Thioguanosine on an Amount of BACE1 Expression under Oxidative Stress Conditions of Brain Nerve Cells In order to determine an influence of chlorhexidine and thioguanosine of the present disclosure on an amount of BACE1 expression under oxidative stress conditions of brain nerve cells, the following experiment was performed.

Brain nerve cells, SH-SY5Y cells, were pretreated with chlorhexidine and thioguanosine at 1 μM, 5 μM, and 10 μM for 24 hours. Then, an oxidative stress substance HNE (4-hydroxynonenal) was applied to the SH-SY5Y cells, and a change in the amount of BACE1 proteins was determined by Western blot. A change in an amount of BACE1 mRNA was determined by real-time PCR.

Figure 7:
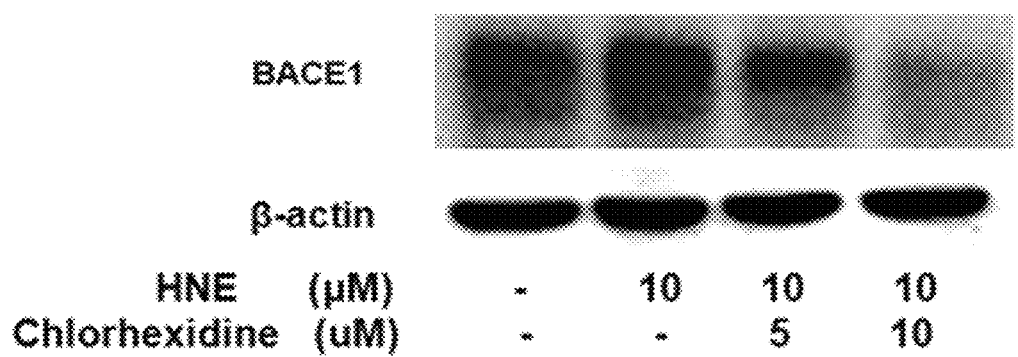
FIG. 7 is a western blot result that shows the result obtained by determining a change in an amount of expression of BACE1 proteins by chlorhexidine treatment under oxidative stress conditions of brain nerve cells in Example 2.
Figure 8:
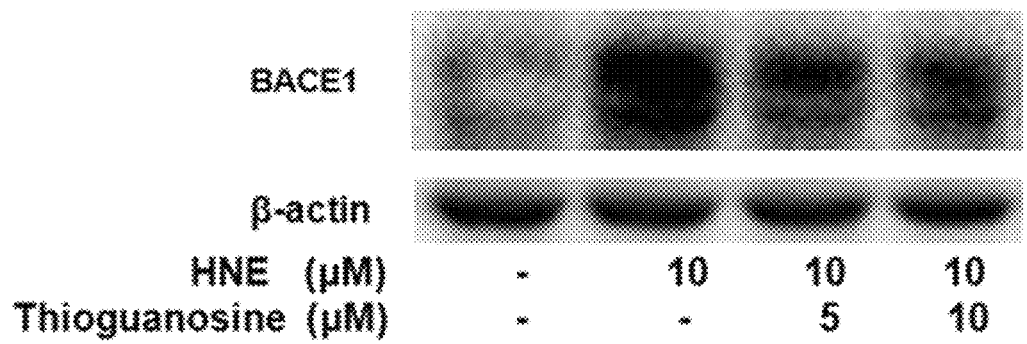
FIG. 8 is a western blot result that shows the result obtained by determining a change in an amount of expression of BACE1 proteins by thioguanosine treatment under oxidative stress conditions of brain nerve cells in Example 2.
Figure 9:
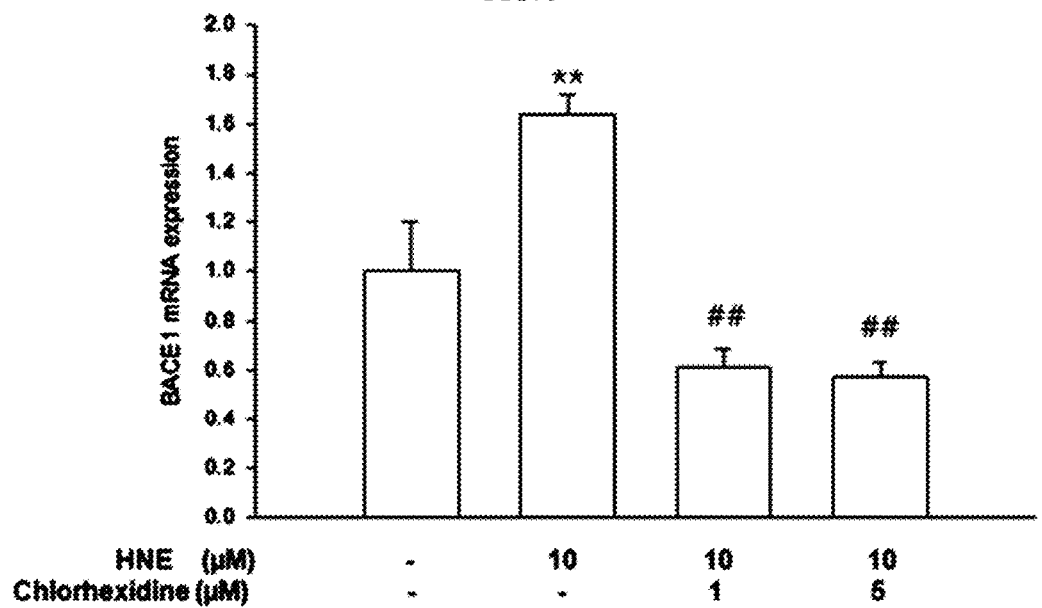
FIG. 9 is a real-time PCR result that shows the result obtained by determining a change in an amount of BACE1 mRNA by chlorhexidine treatment under oxidative stress conditions of brain nerve cells in Example 2.
Figure 10:
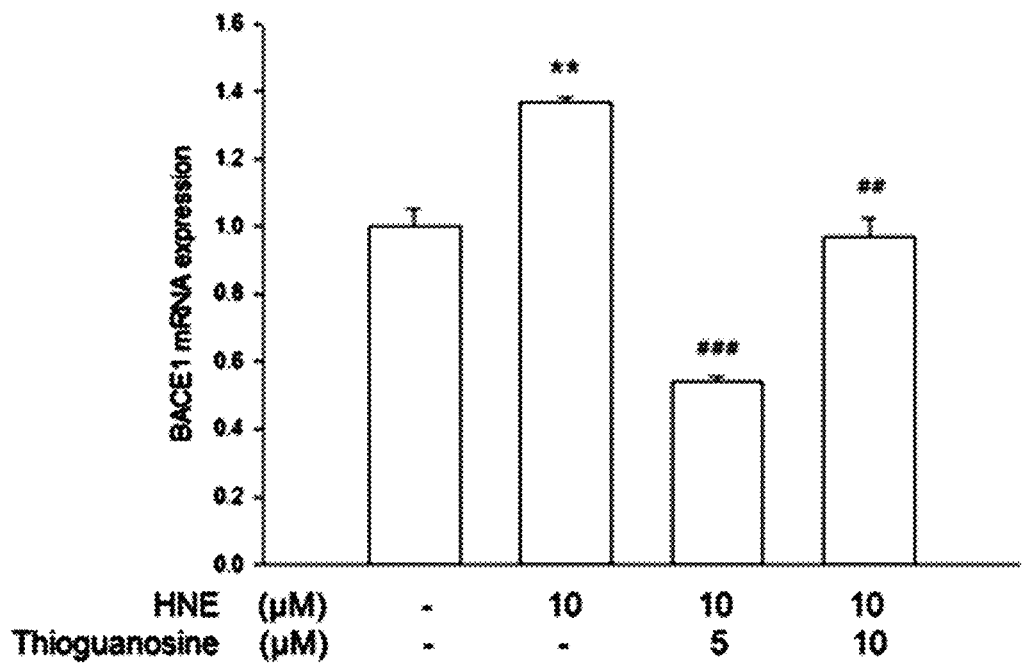
FIG. 10 is a real-time PCR result that shows the result obtained by determining a change in an amount of BACE1 mRNA by thioguanosine treatment under oxidative stress conditions of brain nerve cells in Example 2.

Changes in the amount of expression of BACE1 proteins of chlorhexidine-treated and thioguanosine-treated SH-SY5Y cells under oxidative stress conditions are shown in FIGS. 7 and 8, and changes in the amount of BACE1 mRNA are shown in FIGS. 9 and 10.

As shown in FIGS. 7 to 10, when chlorhexidine or thioguanosine was used as the treatment, an increase in the amount of expression of BACE1 proteins due to oxidative stress decreased at 5 μM and 10 μM (refer to FIGS. 7 and 8). In addition, it could be seen that, when chlorhexidine was used as the treatment, the increase in the amount of BACE1 mRNA due to oxidative stress decreased at 1 μM and at 5 μM (refer to FIG. 9). Similarly, it could be seen that, when thioguanosine was used as the treatment, an increase in the amount of BACE1 mRNA due to oxidative stress decreased at 5 μM and at 10 μM (refer to FIG. 10).

In this regard, in FIGS. 9 and 10, asterisks (**) indicate a significant ($p \leq 0.01$) increase of BACE1 mRNA expression relative to control. Similarly, number signs (##) indicate a significant ($p \leq 0.01$) decrease, and number signs (###) indicate a significant ($p \leq 0.001$) decrease in BACE1 mRNA expression relative to oxidative stress conditions.

Example 3

Verification of an Influence of Chlorhexidine and Thioguanosine on Generation of Amyloid Precursor Protein Carboxy-terminal Fragments (APP CTFs) under Oxidative Stress Conditions of Brain Nerve Cells In order to determine an influence of chlorhexidine and thioguanosine of the present disclosure on APP CTFs under oxidative stress conditions of brain nerve cells, the following experiment was performed.

Brain nerve cells, SH-SY5Y cells, were pretreated with chlorhexidine and thioguanosine at 5 μM and 10 μM for 24 hours. Then, an oxidative stress substance HNE (4-hydroxynonenal) was used as the treatment, and the generation of APP CTFs (C83 and C99) was determined by Western blot. Under oxidative stress conditions of brain nerve cells treated in accordance with the present disclosure, changes in the generation of APP CTFs are shown in FIGS. 11 and 12.

Figure 11:
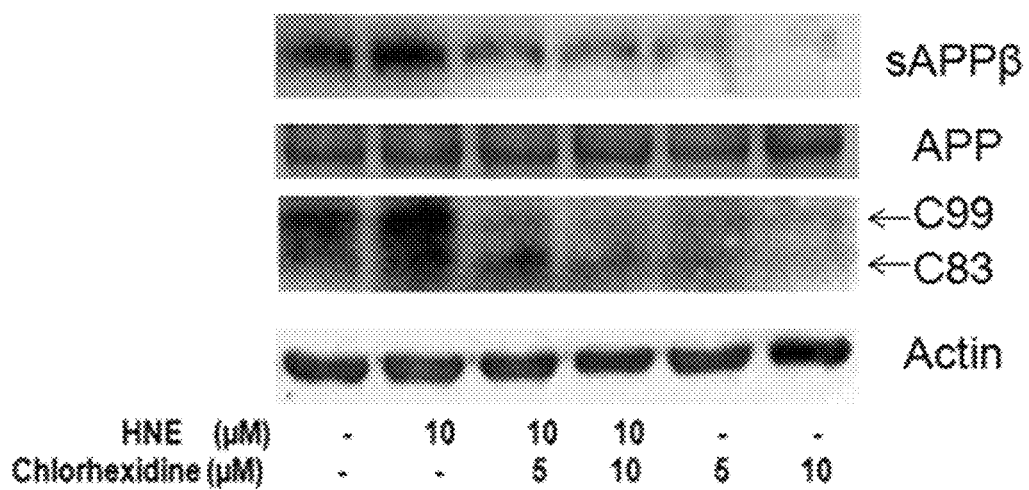
FIG. 11 is a western blot result that shows the result obtained by determining generation of amyloid precursor protein (APP) carboxy-terminal fragments (CTFs) by chlorhexidine treatment under oxidative stress conditions of brain nerve cells in Example 3.

As shown in FIGS. 11 and 12, when chlorhexidine or thioguanosine was used as the treatment, an increase in CTFs due to oxidative stress decreased at 5 μM and 10 μM.

Example 4

Verification of an Influence of Chlorhexidine and Thioguanosine on Learning and Memory in the Alzheimer's Dementia Animal Model In order to determine an influence of chlorhexidine and thioguanosine of the present disclosure on a learning ability and memory in the Alzheimer's dementia animal model, the following experiment was performed.

As an Alzheimer's dementia animal model, 3×Tg-AD mice were used. The 3×Tg-AD mouse is a mouse having overexpressed presenilin, amyloid precursor protein (APP), and Tau genes, which are frequently found in Alzheimer's dementia. The 3×Tg-AD mouse is an animal model that is widely used for research on Alzheimer's dementia (Oddo S. et al, 2003, Neuron, 39, 409-421). 25 mg/kg of chlorhexidine was orally administered every day for 4 weeks; and 0.1 mg/kg and 0.5 mg/kg of thioguanosine were orally administered every day for 8 weeks to 6-month old 3×Tg-AD mice. A Morris water maze test was used to evaluate the effects of chlorhexidine and thioguanosine administration on the mice.

Figure 14:
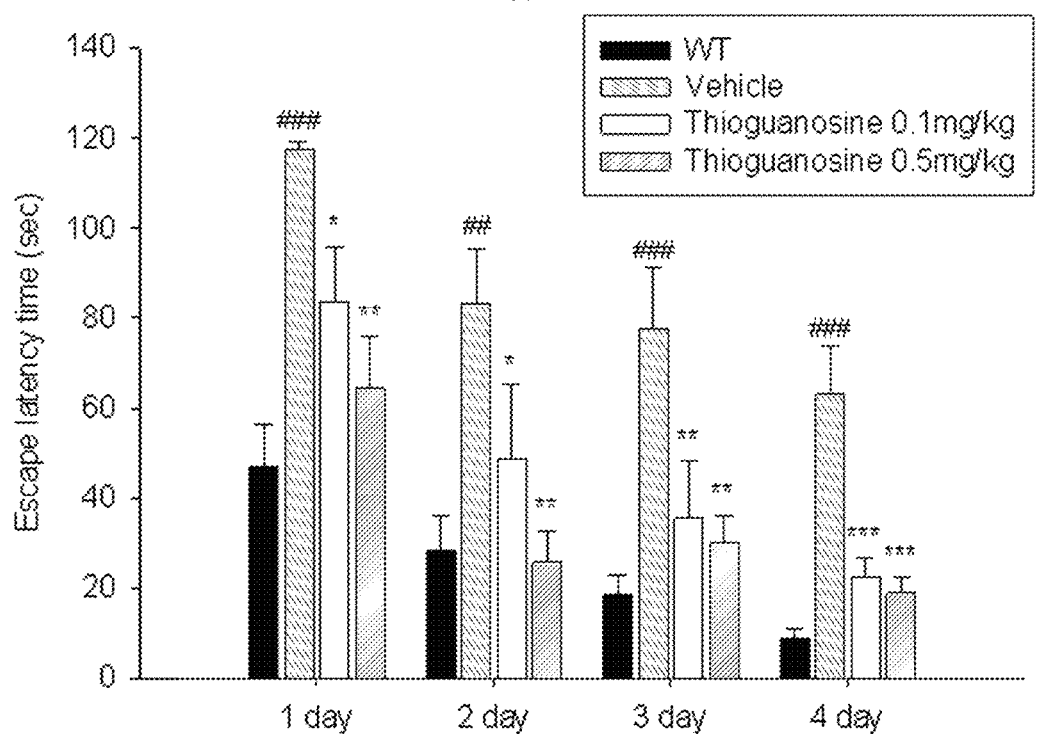
FIG. 14 is a graph that shows the result obtained by determining a change in a learning ability by thioguanosine treatment in an Alzheimer's dementia animal model in Example 4.

In the Morris water maze test, four cues of a star, a rectangle, a triangle, and a circle are attached to walls outside a circular pool (diameter: 100 cm and height: 45 cm), and a platform (diameter: 4.5 cm and height: 14.5 cm) was placed in the pool. Water was filled to 0.5 cm higher than the platform (water temperature 21±1° C.), and food coloring was used to blur the water such that the platform was not visible from the water surface. In this configuration, a treated or control subject was placed into the water with its head towards a water tank wall surface, and a time was recorded for the length of time taken for finding the escape platform. A cut-off time of the mouse was 120 seconds. After 15 minutes, the mouse was placed into the water again, a subsequent time taken for finding the escape platform was recorded, and a change in the learning ability was determined. This procedure was performed over four days, and the result of change in learning ability was measured. FIGS. 13 and 14 show the results.

Figure 15:
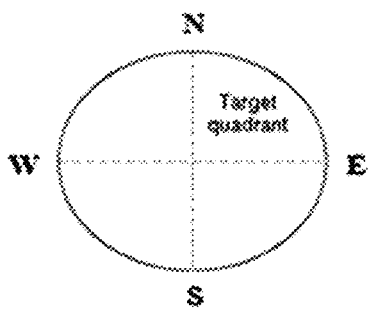
FIG. 15 is a diagram and graph that show the result obtained by determining a change in memory by chlorhexidine treatment in an Alzheimer's dementia animal model in Example 4.
Figure 15:
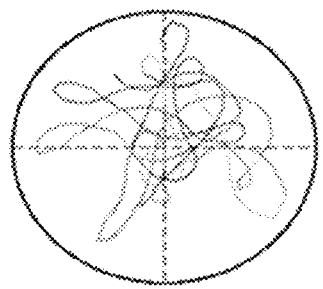
Figure 15:
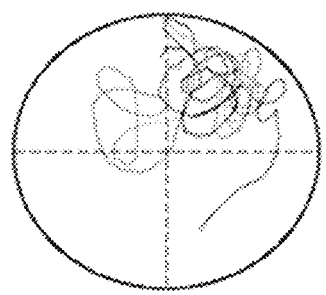
Figure 15:
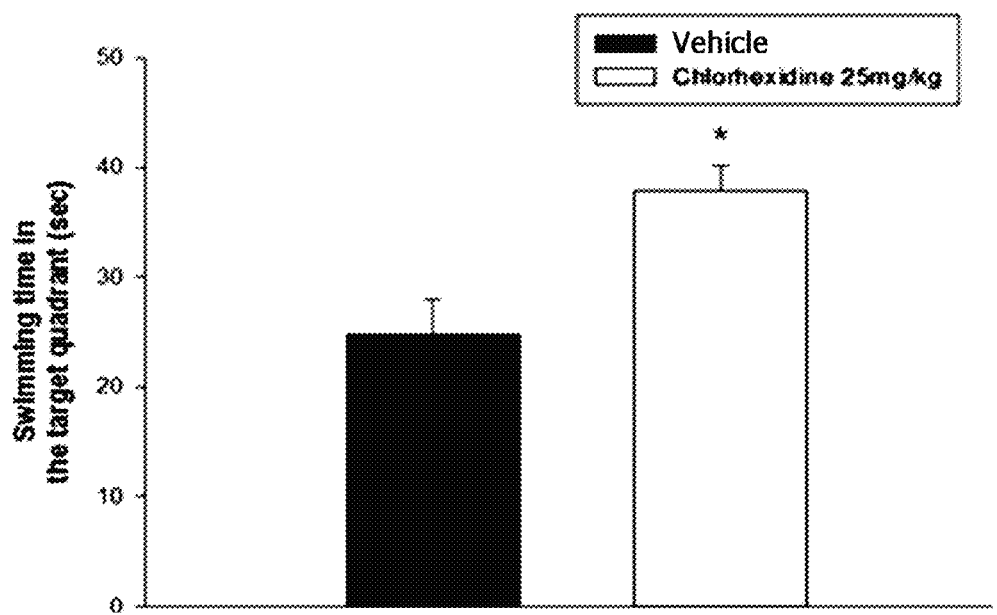
Figure 16:
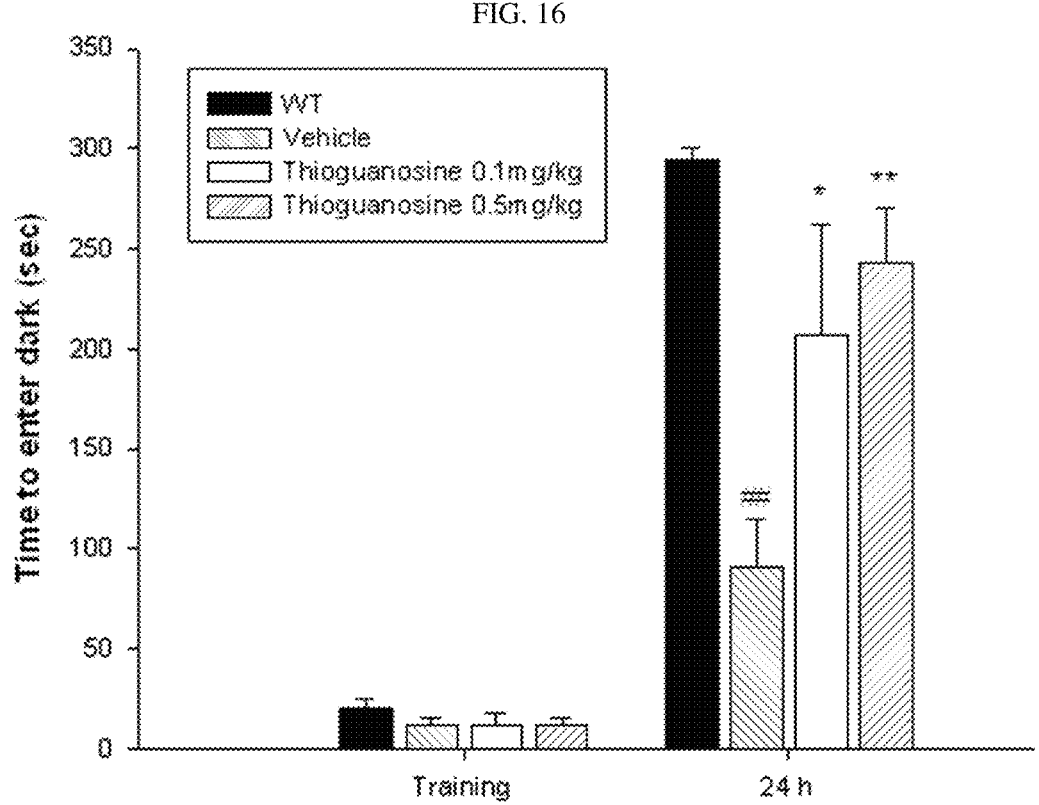
FIG. 16 is a graph that shows the result obtained by determining a change in memory by thioguanosine treatment in an Alzheimer's dementia animal model in Example 4.

As shown in FIGS. 13 and 14, in the Alzheimer's dementia animal model, on the third and fourth days, the mouse to which chlorhexidine was administered showed a faster learning ability for finding the platform than a control group (refer to FIG. 13). In FIGS. 13, 15, 18, 19, and 21, an asterisks (*) indicates a significant ($p \leq 0.05$) difference, asterisks () indicate a significant ($p \leq 0.01$) difference, and asterisks (*) indicate a significant ($p \leq 0.001$) difference from vehicle. From the first day, the mouse to which thioguanosine was administered showed a faster learning ability for finding the platform than the control group (refer to FIG. 14). In FIGS. 14 and 16, number signs (##) indicate a significant ($p \leq 0.01$) difference and number signs (###) indicate a significant ($p \leq 0.001$) difference from wild type. Similarly, asterisks () indicate a significant ($p \leq 0.01$) difference and asterisks (*) indicate a significant ($p \leq 0.001$) difference from vehicle.

In addition, the platform was removed from the pool on the fifth day. The subjects were then provided a time of 60 seconds in the pool to measure certain changes in memory. FIG. 15 shows the result.

As shown in FIG. 15, in the Alzheimer's dementia animal model without treatment, a subject demonstrated no obvious preference for the target quadrant, which formerly held the platform. In contrast, the chlorhexidine-treated subjects of the Alzheimer's dementia animal model spent the majority of time in the location in which the platform was formerly placed.

In addition, a passive avoidance test was performed on a thioguanosine-administered 3×Tg-AD mouse. More specifically, when the mouse was put into a step-through device and went into a dark box, electric shocks (0.5 mA and 2 seconds) were applied for learning. After 24 hours, the mouse was put into a bright box again and a time taken for entering the black box was measured to measure changes in learning and memory. FIG. 16 shows the result.

As shown in FIG. 16, in the Alzheimer's dementia animal model, the mouse to which thioguanosine was administered remembered the electric shock in the dark place, and spent a longer time in the bright box and therefore it could be seen that memory had increased.

Figure 17:
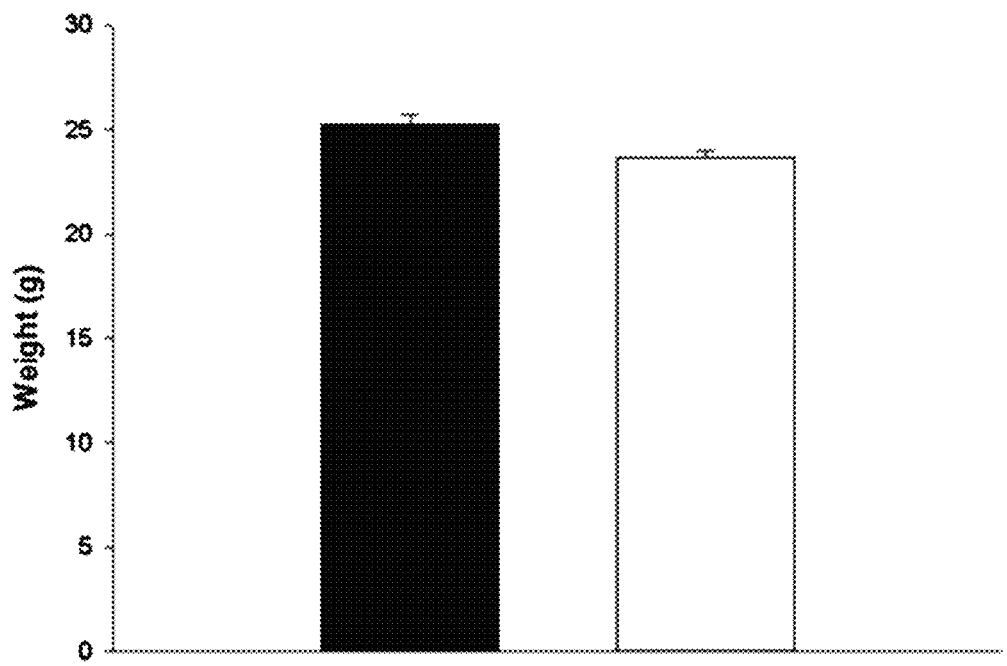
FIG. 17 is a graph that shows the result obtained by determining changes in a body weight, and weights of a brain, a heart, a liver, and a kidney after chlorhexidine treatment in an Alzheimer's dementia animal model in Example 4.
Figure 17:
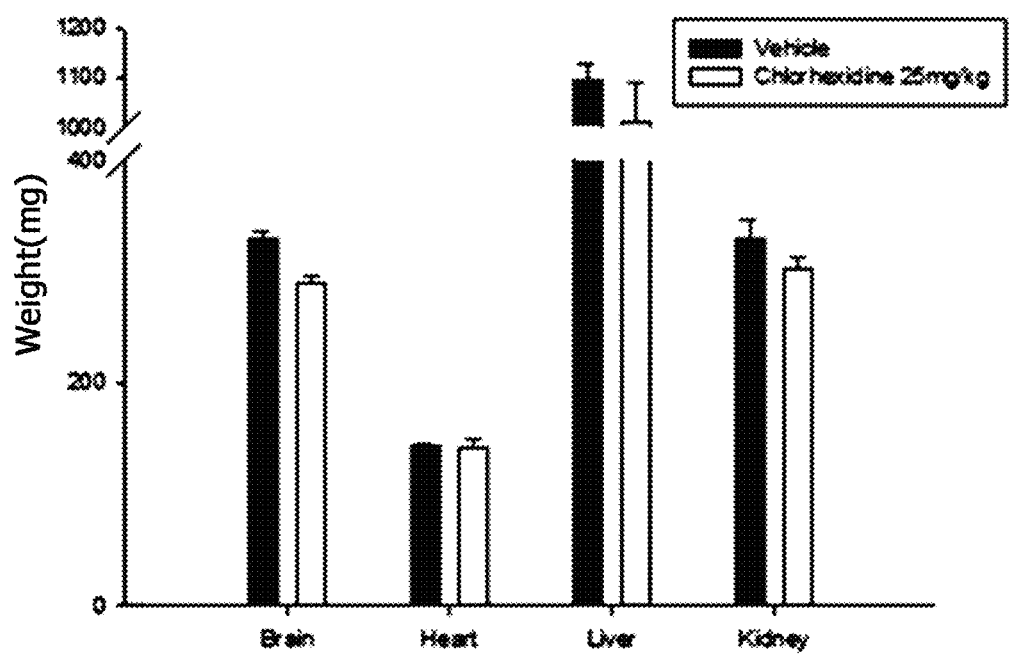

In order to evaluate potential toxicity of chorhexidine, the body weights and weights of organs were measured for treatment and vehicle subjects. FIG. 17 shows the result.

As shown in FIG. 17, in the Alzheimer's dementia animal model, the chlorhexidine treatment group had body weights and organ weights similar to those of the control group, and no toxicity was determined Example 5

Verification of an Influence of Chlorhexidine on an Amount of BACE1 Expression in the Alzheimer's Dementia Animal Model In order to determine an influence of chlorhexidine of the present disclosure on an amount of BACE1 expression in the Alzheimer's dementia animal model, the following experiment was performed.

Figure 18:
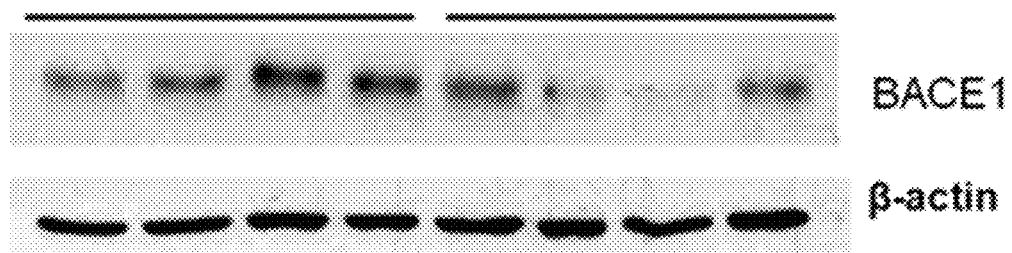
FIG. 18 is a western blot result and a graph that show the result obtained by determining a change in an amount of expression of BACE1 proteins by chlorhexidine treatment in a brain of an Alzheimer's dementia animal model in Example 5.
Figure 18:
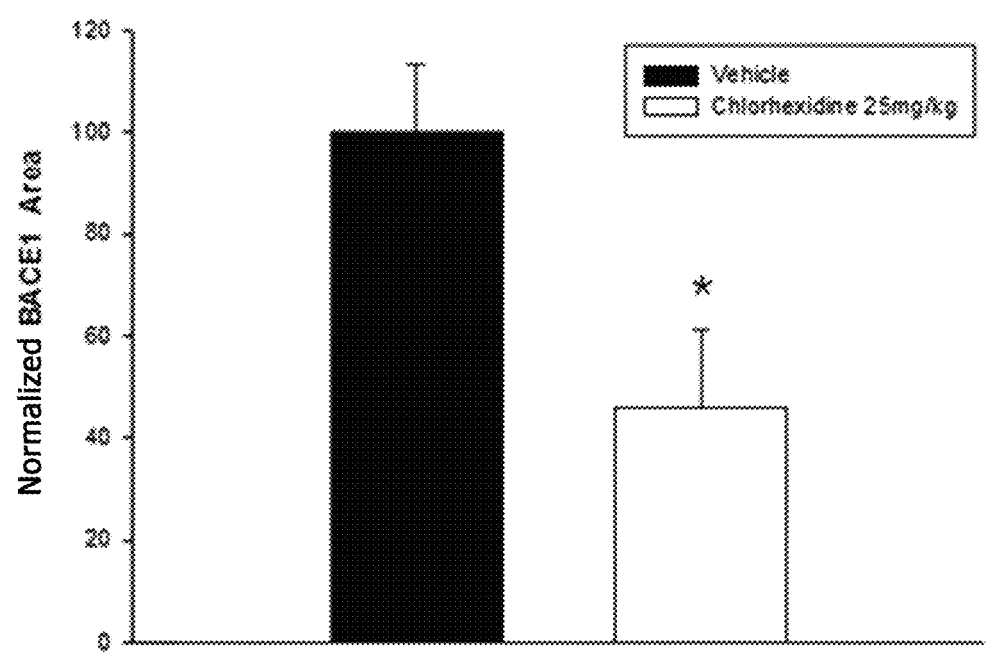
Figure 19:
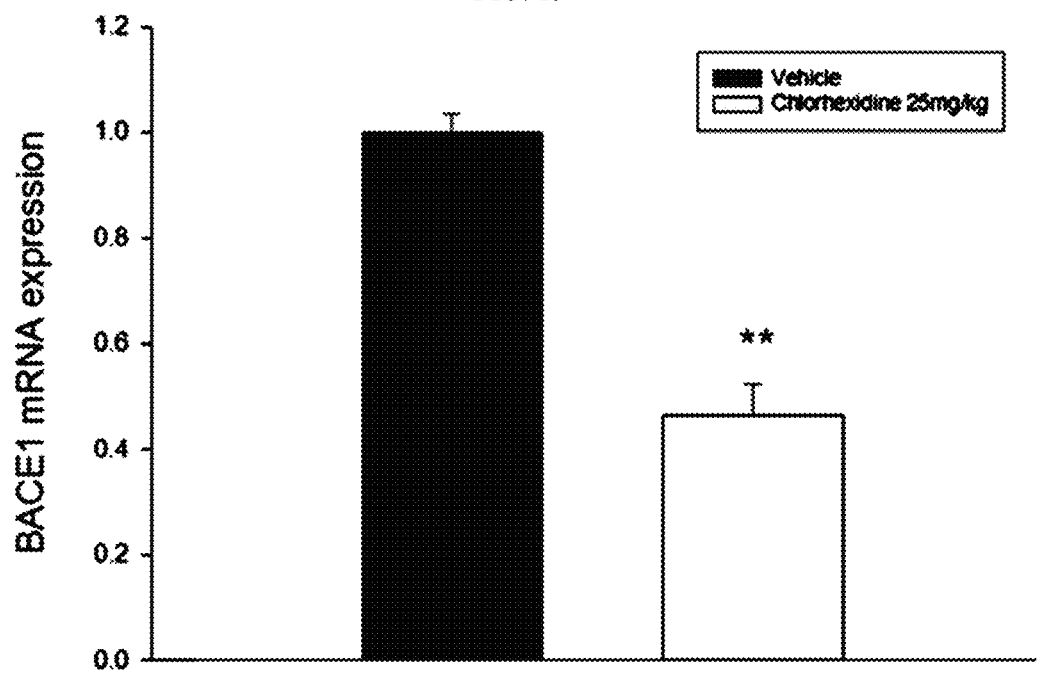
FIG. 19 is a real-time PCR result that shows the result obtained by determining a change in an amount of BACE1 mRNA by chlorhexidine treatment in a brain of an Alzheimer's dementia animal model in Example 5.

From the 3×Tg-AD mouse to which chlorhexidine was administered in Example 4a brain was extracted. The extracted brain was lysed using a tissue lysis buffer and RNA was extracted using Trizol. The amount of BACE1 expression was determined by Western blot and real-time PCR. FIGS. 18 and 19 show the results.

As shown in FIGS. 18 and 19, in the Alzheimer's dementia animal model, a brain of a chlorhexidine-treated subject showed lower expression of BACE1 proteins than that of the control group (refer to FIG. 18), and showed a lower amount of BACE1 mRNA than that of the control group (refer to FIG. 19).

Example 6

Verification of an Influence of Chlorhexidine on Generation of Aβ in the Alzheimer's Dementia Animal Model In order to determine an influence of chlorhexidine of the present disclosure on generation of Aβ in the Alzheimer's dementia animal model, the following experiment was performed.

Figure 20:
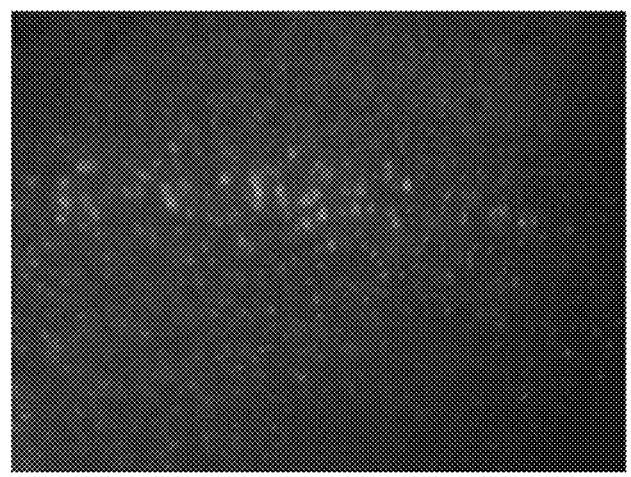
FIG. 20 is an immuno staining result that shows regulation of an amount of Aβ by chlorhexidine treatment in a brain (cortex) of an Alzheimer's dementia animal model in Example 6 using immuno staining.
Figure 20:
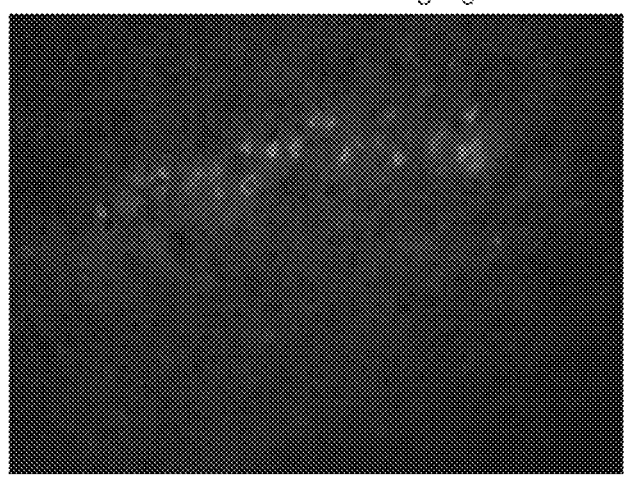
Figure 21:
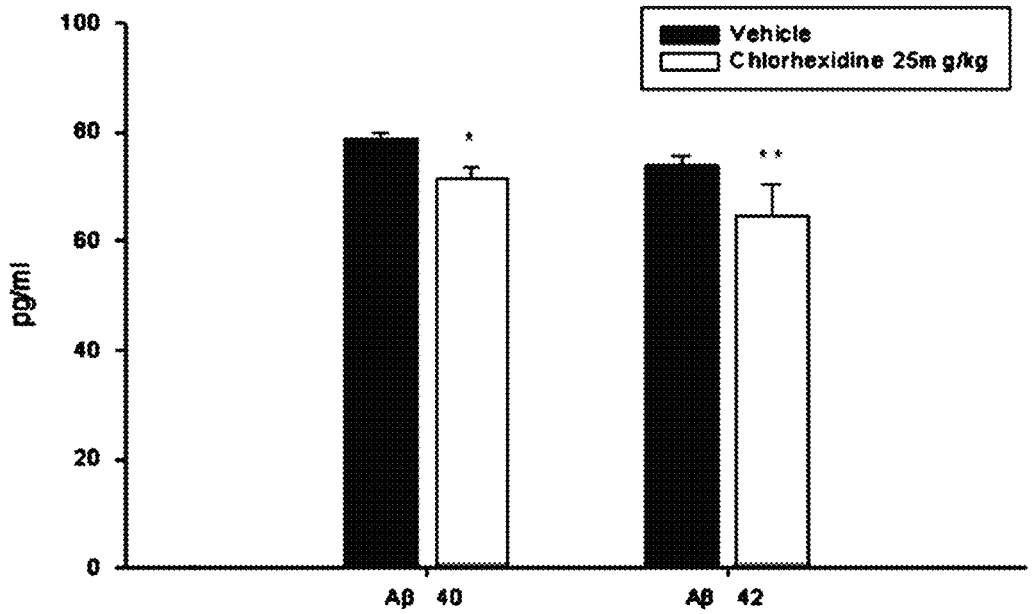
FIG. 21 is a human amyloid β assay kit result that shows regulation of an amount of Aβ by chlorhexidine treatment in a brain of an Alzheimer's dementia animal model in Example 6 using ELISA.

From the 3×Tg-AD mouse to which chlorhexidine was administered in Example 4a brain was extracted. A 40 nm frozen section was prepared from the extracted brain using a microtome. Then, generation of Aβ was measured using immuno staining or a human amyloid 13 (1-40) assay kit (IBL) and a human amyloid β (1-42) assay kit (IBL). FIGS. 20 and 21 show the results.

As shown in FIGS. 20 and 21, in the Alzheimer's dementia animal model, a cortex part of a brain of the mouse to which chlorhexidine was administered showed lower generation of Aβ than that of the control group (refer to FIG. 20). In particular, it could be seen that generation of Aβ40 and Aβ42 decreased (refer to FIG. 21).

Example 7

Verification of an Influence of Chlorhexidine, Thioguanosine, Mebendazole, Colchicine, Farnesol, Trimethobenzamide Hydrochloride, Disulfuram, Azathioprine, Mebeverine Hydrochloride, Efavirenz, Thiostrepton, Probenecid, Entacapone, Harmine Hydrochloride, Flunisolide, Thimerosal, Hexestrol, Sulfaquinoxaline Sodium Salt, Monensin Sodium Salt, Raloxifene Hydrochloride, 2-Chloropyrazine, and Topotecan on a BACE1 Promoter Activity in Brain Nerve Cells In order to determine an influence of chlorhexidine, thioguanosine, mebendazole, colchicine, farnesol, trimethobenzamide hydrochloride, disulfuram, azathioprine, mebeverine hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan of the present disclosure on the BACE1 promoter activity in brain nerve cells, the following experiment was performed.

Figure 22:
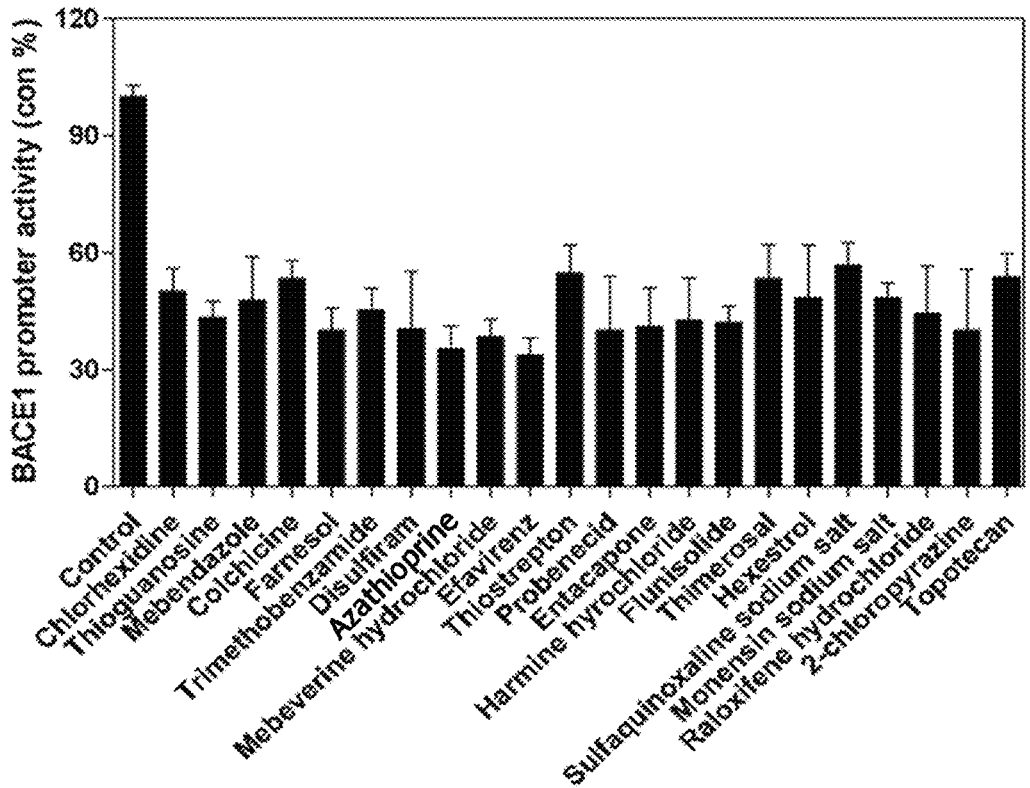
FIG. 22 is a diagram that shows the result obtained by determining a change in a BACE1 promoter activity by treatment of chlorhexidine, thioguanosine, mebendazole, fenbendazole, colchicine, farnesol, trimethobenzamide hydrochloride, disulfuram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan in brain nerve cells in Example 7.

A BACE1 promoter-luciferase vector was transfected to brain nerve cells (SH-SY5Y). Then, chlorhexidine, thioguanosine, mebendazole, colchicine, farnesol, trimethobenzamide hydrochloride, disulfuram, azathioprine, mebeverine hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan were used as treatments at 10 μM for 24 hours. A change in a BACE1 promoter activity was measured using a Dual-Luciferase assay kit. FIG. 22 shows the result.

As shown in FIG. 22, when chlorhexidine, thioguanosine, mebendazole, colchicine, farnesol, trimethobenzamide hydrochloride, disulfuram, azathioprine, mebeverine hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan are used as treatments, it could be seen that the BACE1 promoter activity decreased by 50% or more.

Chlorhexidine, thioguanosine, mebendazole, fenbendazole, colchicine, farnesol, and the like, which are the active ingredients of the composition according to the present disclosure, decrease expression of BACE1 proteins, induce improvement of learning and memory in Alzheimer's dementia animals, and suppress generation of Aβ causing apoptosis of brain nerve cells. Therefore, the composition according to the present disclosure may be usefully used as a composition for preventing, improving, or treating diabetes or brain diseases related to Alzheimer's dementia, and additionally, may be expected to be usefully used as a health functional food composition.

The above description of the disclosure is only exemplary, and it will be understood by those skilled in the art that various modifications can be made in other concrete forms without departing from the scope of the present disclosure and without changing essential features. Therefore, the above-described examples should be considered in a descriptive sense only and not for purposes of limitation.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Therefore, the scope of the disclosure is defined not by the detailed description, but by the claims and their equivalents, and all variations within the scope of the claims and their equivalents are to be construed as being included in the disclosure.

What is claimed is:

1. A method for treating Alzheimer's dementia (Alzheimer's disease), comprising administering a pharmaceutical composition to a subject in need of treatment for Alzheimer's dementia (Alzheimer's disease),
   wherein the pharmaceutical composition is administered in an amount effective to decrease expression of BACE1 proteins, and
   wherein the pharmaceutical composition comprises at least one active ingredient selected from the group consisting of chlorhexidine, thioguanosine, mebendazole, fenbendazole, colchicine, farnesol, trimethobenzamide hydrochloride, disulfiram, azathioprine, mebeverine hydrochloride, zaprinast, tosufloxacin hydrochloride, efavirenz, thiostrepton, probenecid, entacapone, harmine hydrochloride, flunisolide, thimerosal, hexestrol, sulfaquinoxaline sodium salt, monensin sodium salt, raloxifene hydrochloride, 2-chloropyrazine, and topotecan.

2. The method of claim 1,
   wherein the active ingredient is a guanidine compound selected from the group consisting of chlorhexidine, thioguanosine, mebendazole, and fenbendazole.

3. The method of claim 1,
   wherein the active ingredient is chlorhexidine or thioguanosine.

4. The method of claim 1,
   wherein the pharmaceutical composition suppresses generation of amyloid beta peptides (Aβ).

5. The method of claim 1,
   further comprising a step of measuring expression of BACE1 proteins, wherein the pharmaceutical composition is administered in an amount effective to decrease expression of BACE1 proteins compared to the measured expression of BACE1 proteins.

* * * * *